(12) United States Patent
Abeyrathne et al.

(10) Patent No.: US 12,019,045 B2
(45) Date of Patent: Jun. 25, 2024

(54) ION SELECTIVE SENSOR

(71) Applicant: MX3 Diagnostics, Inc., Austin, TX (US)

(72) Inventors: Chathurika Darshani Abeyrathne, Mitcham (AU); You Liang, Carlton (AU); Efstratios Skafidas, Thornbury (AU)

(73) Assignee: MX3 Diagnostics, Inc., Austin, TX (US)

( * ) Notice: Subject to any disclaimer, the term of this patent is extended or adjusted under 35 U.S.C. 154(b) by 746 days.

(21) Appl. No.: 16/598,000

(22) Filed: Oct. 10, 2019

(65) Prior Publication Data

US 2020/0116664 A1    Apr. 16, 2020

Related U.S. Application Data

(60) Provisional application No. 62/744,389, filed on Oct. 11, 2018.

(51) Int. Cl.
*G01N 27/333* (2006.01)
*G01N 27/327* (2006.01)
*G01N 33/543* (2006.01)

(52) U.S. Cl.
CPC ..... *G01N 27/3335* (2013.01); *G01N 27/3275* (2013.01); *G01N 33/54366* (2013.01)

(58) Field of Classification Search
None
See application file for complete search history.

(56) References Cited

U.S. PATENT DOCUMENTS

| 3,979,274 A | 9/1976 | Newman |
| 5,222,936 A | 6/1993 | Stephen et al. |
| 5,282,950 A | 2/1994 | Dietze et al. |
| 5,685,319 A | 11/1997 | Marett |

(Continued)

FOREIGN PATENT DOCUMENTS

| CN | 109682878 A | 4/2019 |
| EP | 1710565 | 10/2006 |

(Continued)

OTHER PUBLICATIONS

A. Moya, et al., "Flexible Microfluidic Bio-Lab-on-a-Chip Multi-Sensor Platform for Electrochemical Measurements", SENSORS, 2014 IEEE, pp. 1018-1021 (Year: 2014).*

(Continued)

*Primary Examiner* — J. Christopher Ball
(74) *Attorney, Agent, or Firm* — Knobbe, Martens, Olson & Bear LLP

(57) ABSTRACT

An ion sensor includes a substrate, at least one ion selective electrode deposited on the substrate, and a reference electrode deposited on the substrate. The sensor may further include an insulating layer placed over the ion selective electrode and the reference electrode and having openings for the ion selective electrode and the reference electrode, a microfluidic layer placed over at least part of the insulating layer, and a cover layer placed over the microfluidic layer. The reference electrode includes reference electrode material deposited on the substrate and a combination of a polymer and a chloride-containing salt deposited on the reference electrode material.

31 Claims, 11 Drawing Sheets

(56) References Cited

U.S. PATENT DOCUMENTS

| | | | |
|---|---|---|---|
| 5,714,341 A | 2/1998 | Thieme et al. |
| 5,776,783 A | 7/1998 | Kell |
| 5,908,788 A | 6/1999 | Kell |
| 6,086,748 A | 7/2000 | Durst et al. |
| 6,102,872 A | 8/2000 | Doneen et al. |
| 6,315,951 B1 | 11/2001 | Markart |
| 6,377,896 B1 | 4/2002 | Sato et al. |
| 6,464,848 B1 | 10/2002 | Matsumoto |
| 6,554,982 B1 | 4/2003 | Shin et al. |
| 8,399,259 B2 | 3/2013 | Fukunaga et al. |
| 8,465,635 B2 | 6/2013 | Thuerlemann et al. |
| 9,546,973 B2 | 1/2017 | McIlrath |
| 9,713,440 B2 | 7/2017 | Hurd et al. |
| 10,197,523 B2 | 2/2019 | Huang et al. |
| 10,258,278 B2 | 4/2019 | Howell et al. |
| 10,989,724 B1 | 4/2021 | Holmes et al. |
| 11,219,410 B2 | 1/2022 | Cheuvront |
| 11,690,566 B2 | 7/2023 | Skafidas et al. |
| 11,701,036 B2 | 7/2023 | Nguyen et al. |
| 11,703,436 B2 | 7/2023 | Skafidas et al. |
| 2001/0032785 A1 | 10/2001 | Cha et al. |
| 2002/0011408 A1 | 1/2002 | Lee et al. |
| 2002/0060247 A1 | 5/2002 | Krishnaswamy et al. |
| 2002/0065332 A1 | 5/2002 | Choi et al. |
| 2003/0150745 A1 | 8/2003 | Teodorczyk et al. |
| 2003/0159948 A1* | 8/2003 | Benco ............... G01N 27/3335 |
| | | 204/418 |
| 2003/0171697 A1 | 9/2003 | Smith et al. |
| 2003/0213691 A1* | 11/2003 | Peper ............... G01N 27/3335 |
| | | 204/418 |
| 2004/0173458 A1 | 9/2004 | Noda et al. |
| 2004/0232009 A1 | 11/2004 | Okuda et al. |
| 2004/0238358 A1 | 12/2004 | Forrow et al. |
| 2005/0023152 A1 | 2/2005 | Surridge et al. |
| 2005/0143675 A1 | 6/2005 | Neel et al. |
| 2005/0201895 A1 | 9/2005 | Donsky |
| 2005/0279647 A1 | 12/2005 | Beaty |
| 2006/0137980 A1 | 6/2006 | Lauks et al. |
| 2007/0015287 A1 | 1/2007 | Robbins et al. |
| 2007/0048224 A1 | 3/2007 | Howell et al. |
| 2007/0073127 A1 | 3/2007 | Kiani et al. |
| 2007/0098600 A1 | 5/2007 | Kayyem |
| 2007/0272564 A1 | 11/2007 | Huang |
| 2008/0118397 A1 | 5/2008 | Slowey et al. |
| 2009/0024060 A1 | 1/2009 | Darrigrand et al. |
| 2009/0173629 A1 | 7/2009 | Kidwell |
| 2010/0176006 A1 | 7/2010 | Bickford et al. |
| 2010/0249652 A1 | 9/2010 | Rush et al. |
| 2011/0162978 A1 | 7/2011 | Cardosi et al. |
| 2012/0067741 A1 | 3/2012 | Kranendonk et al. |
| 2012/0083711 A1 | 4/2012 | Goldstein et al. |
| 2012/0109011 A1 | 5/2012 | Cogan et al. |
| 2012/0165626 A1 | 6/2012 | Irina et al. |
| 2012/0282616 A1 | 11/2012 | Zeijlstra et al. |
| 2012/0289863 A1 | 11/2012 | Goldstein et al. |
| 2013/0069120 A1 | 3/2013 | Merz et al. |
| 2013/0199944 A1 | 8/2013 | Petisee |
| 2013/0233061 A1 | 9/2013 | Sullivan |
| 2013/0341186 A1 | 12/2013 | Hsu |
| 2014/0105788 A1 | 4/2014 | Iwamoto et al. |
| 2014/0277291 A1 | 9/2014 | Pugh et al. |
| 2014/0326037 A1 | 11/2014 | Fukuda et al. |
| 2015/0091592 A1 | 4/2015 | Elder |
| 2015/0216471 A1 | 8/2015 | Goldstein et al. |
| 2015/0217115 A1 | 8/2015 | Avitall |
| 2015/0226695 A1 | 8/2015 | Bakker et al. |
| 2015/0226752 A1 | 8/2015 | Nazareth et al. |
| 2015/0289790 A1 | 10/2015 | Swenson |
| 2015/0359458 A1 | 12/2015 | Erickson et al. |
| 2016/0011178 A1 | 1/2016 | Hoenes et al. |
| 2016/0045144 A1 | 2/2016 | Bansal et al. |
| 2016/0120468 A1 | 5/2016 | Mathew et al. |
| 2016/0266102 A1 | 9/2016 | Knopfmacher |
| 2016/0320326 A1 | 11/2016 | Zevenbergen |
| 2016/0361001 A1 | 12/2016 | Tai et al. |
| 2017/0014822 A1 | 1/2017 | Ker |
| 2017/0027506 A1 | 2/2017 | Howell et al. |
| 2017/0067889 A1 | 3/2017 | Tamir |
| 2017/0138962 A1 | 5/2017 | Southern |
| 2017/0261461 A1 | 9/2017 | Bychkova et al. |
| 2018/0125400 A1 | 5/2018 | Yang et al. |
| 2018/0220947 A1 | 8/2018 | Bedell, Jr. |
| 2019/0150836 A1 | 5/2019 | Skafidas |
| 2020/0011851 A1 | 1/2020 | Piasio et al. |
| 2020/0383582 A1 | 12/2020 | Bychkov |
| 2021/0005233 A1 | 1/2021 | Kim et al. |
| 2021/0005322 A1 | 1/2021 | Huynh et al. |
| 2021/0007646 A1 | 1/2021 | Nguyen et al. |
| 2021/0215662 A1 | 7/2021 | Erlichster et al. |
| 2021/0223239 A1 | 7/2021 | De et al. |
| 2021/0239586 A1 | 8/2021 | Skafidas et al. |
| 2022/0013212 A1 | 1/2022 | Tseng et al. |
| 2022/0122743 A1 | 4/2022 | Erlichster et al. |
| 2022/0143609 A1 | 5/2022 | Xu et al. |

FOREIGN PATENT DOCUMENTS

| | | |
|---|---|---|
| EP | 2075339 A1 | 7/2009 |
| JP | 2002-540424 A | 11/2002 |
| JP | 2014-095692 A | 5/2014 |
| JP | 2017-532571 A | 11/2017 |
| KR | 20160035584 A | 3/2016 |
| KR | 10-2019-0127349 A | 11/2019 |
| WO | 98/12557 A1 | 3/1998 |
| WO | 00/58720 A1 | 10/2000 |
| WO | WO2010045247 A1 | 4/2010 |
| WO | WO2011075711 A1 | 6/2011 |
| WO | 2012/012135 A2 | 1/2012 |
| WO | 2013/075711 A1 | 5/2013 |
| WO | WO2014176753 | 11/2014 |
| WO | 2016/069935 A1 | 5/2016 |
| WO | 2018/004191 A1 | 1/2018 |
| WO | 2018/191322 A1 | 10/2018 |

OTHER PUBLICATIONS

R.B.P. Elmes & K.A. Jolliffe, "Anion recognition by cyclic peptides", Chem. Commun., 51(24): p. 4951-4968 (Year: 2015).*

P. Bühlmann, E. Pretsch, & E. Bakker, "Carrier-Based Ion-Selective Electrodes and Bulk Optodes. 2. Ionophores for Potentiometric and Optical Sensors", Chem. Rev., 98(4): p. 1593-1688, Jun. 1998.*

International Search Report and Written Opinion for PCT Application No. PCT/US2019/055607, dated Jan. 21, 2020, 17 pages.

Oncescu et al., "Smartphone based health accessory for colorimetric detection of biomarkers in sweat and saliva," Lab on a Chip 13(16):3232-3238, Jun. 7, 2013.

"Cepheid and Sherlock Biosciences Establish Collaboration on New GeneXpert Tests for Infectious Diseases and Oncology Leveraging CRISPR Technology, http://cepheid.mediaroom.com/2020-02-28-Cepheid-and-Sherlock-Biosciences-Establish-Collaboration-on-New-GeneXpert-Tests-for-Infectious-Diseases-and-Oncology-Leveraging-CRISPR-Technology, 3 pages (Feb. 28, 2020)."

"Cepheid, Xpert Carba-R, GXCARBAR-10, https://www.cepheid.com/Package%20Insert20Files/Xpert-Carba-R-RX-Only-US-IVD-ENGLISH-Package-Insert-301-2438-Rev-F.pdf, Rev. F, 54 pages (Aug. 2019)."

Erlichster et al., "Assessment of Biomarker Concentration in a Fluid," U.S. Appl. No. 62/961,438, filed Jan. 15, 2020, 22 pages.

Erlichster et al., "Pan-Family Assays for Rapid Viral Screening: Reducing Delays in Public Health Responses During Pandemics", Clinical Infectious Diseases, Jul. 20, 2020 (Jul. 20, 2020), pp. 1-6, XP055830068.

Erlichster et al., "Personalized Hydration Assessment and Fluid Replenishment," U.S. Appl. No. 62/876,263, filed Jul. 19, 2019, 30 pages.

Erlichster et al., "Personalized Hydration Assessment and Fluid Replenishment," U.S. Appl. No. 62/957,527, filed Jan. 6, 2020, 35 pages.

International Preliminary Report on Patentability and Written Opinion, re PCT Application No. PCT/US2019/055607, dated Apr. 22, 2021.

(56) References Cited

OTHER PUBLICATIONS

Nguyen et al., "Saliva Test Strip and Method" U.S. Appl. No. 62/872,339, filed Jul. 10, 2019, 31 pages.
Paul K et al., "The arrival of a true point-of-care molecular assay-ready for global implementation?", Nov. 1, 2015 (Nov. 1, 2015), pp. e663-e664, XP055830065.
Skafidas et al., "Biological Fluid Sample Assessment," U.S. Appl. No. 62/967,694, filed Jan. 30, 2020, 21 pages.
Joseph, C., et al., "Use of an algorithm applied to urine drug screening to assess adherence to an oxycontin regimen", Journal Of Opioid Management, vol. 5, No. 6, Nov. 1, 2009, pp. 359-364.

* cited by examiner

ION SELECTIVE SENSOR

TECHNICAL FIELD

The present disclosure relates to the field of electrochemical sensors. More specifically, the application is directed to an improved reference electrode for electrochemical measurements, as well as the ion sensor itself and a method of making the sensor.

BACKGROUND OF THE INVENTION

Electrochemical sensors may be used in a wide variety of devices for many different purposes. For example, ion sensors may be used for detecting and/or measuring one or more ions in a solution. A pH sensor is just one example of such electrochemical sensors. Ion sensors typically work by generating voltages that scale with the concentration of an ion in the solution being tested. An ion sensor typically includes one or more ion-selective electrodes (ISEs) and a reference electrode. The reference electrode has an applied potential that is used as a reference potential for the ISE system configuration. The potential difference between the ISE and the reference electrode acts as a measure of the concentration of the ion (or multiple ions) being tested.

To use an ion sensor, the reference electrode and the ion-selective electrodes are fully covered with the solution being tested, to create a bridge between the ISEs and the reference electrode. For the sensor to work properly, the potential of the reference electrode should be stable, constant and independent of the concentration and composition of the solution. A commonly used type of reference electrode is made up of a silver chloride electrode (Ag/AgCl) material immersed in a 3 molar potassium chloride (KCl) solution. This type of reference electrode is bulky and requires a relatively large volume of sample solution. Most planar reference electrodes include a hydrogel on top of a screen-printed Ag/AgCl electrode. This type of planar reference electrode, however, requires conditioning of the electrode (for example loading of KCl) for several hours before the sensor can be used. Thus, these types of reference electrodes are not suitable for disposable ion sensors or other ion sensors where it is not practical to go through the conditioning step. Additionally, currently available ion sensors need to be calibrated with a known concentration of ion solutions before use—a time consuming process.

Therefore, it would be desirable to have improved ISEs and reference electrodes for ion sensors. Ideally, an improved reference electrode would be small enough to be usable on a planar electrode, would require only a small volume of sample, and would not require conditioning of the electrode. It would also be desirable to have an improved reference electrode that provided for long term stability and storage. Such an electrode would make an ion sensor more readily disposable and accessible for users. At least some of these objectives will be addressed in the present application.

BRIEF SUMMARY

The present application generally describes an improved reference electrode, an improved ion sensor that includes the reference electrode, and methods for making the improved reference electrode and the improved ion sensor.

In one aspect of the present disclosure, an ion sensor includes: a substrate including a non-conductive material; at least one ion selective electrode including a ion selective electrode material deposited on the substrate; a reference electrode; an insulating layer placed over the ion selective electrode and the reference electrode, the insulating layer comprising at least one opening for each of the at least one ion selective electrode and the reference electrode; a microfluidic layer placed over at least part of the insulating layer; and a cover layer placed over the microfluidic layer. The reference electrode includes a reference electrode material deposited on the substrate and a combination of a chloride-containing salt and a polymer deposited on the reference electrode material.

In some embodiments, the cover layer may include at least one exit pore and an inlet lip. The ion sensor may include a filter material layer positioned on top of the insulation layer or between the microfluidic layer and the cover layer. The filter material layer may include a material such as but not limited to filter paper, hydrophilic mesh, hydrophilic membrane or cotton wool (or "cotton batting") to guide the fluids. In some embodiments, the ion sensor includes an ion-selective membrane disposed over part of the at least one ion selective electrode. The ion-selective membrane may include an ionophore cocktail that includes an ionophore, such as but not limited to potassium ionophore, calcium ionophore, sodium ionophore, magnesium ionophore, hydrogen ionophore, nitrate ionophore, or ammonium ionophore.

In some embodiments, the ion-selective membrane includes a ion/molecular imprinted polymer to detect ions in an electrolyte solution or molecules in a sample. In another embodiment, the ion selective membrane can be functionalized with antibody or may include antibody embedded polymer to detect proteins. In some embodiments, the ion-selective membrane is an antibody selective membrane which includes a linker to detect specific antibodies in a sample solution. Some embodiments may further include a transducing material layer disposed between the at least one ion selective electrode material and the ion-selective membrane. For example, the transducing material layer may include, but is not limited to, poly(3,4-ethylenedioxythiophene) polystyrene sulfonate (PEDOT:PSS), polypyrrole (PPy), polyaniline (PANI), or carbon nanotubes.

In some embodiments, the ion selective electrode is configured to detect pH of a solution, and the ion selective electrode material is a metal oxide. In some embodiments, the ion selective electrode material is a metal oxide with an ion selective membrane to detect ions of an electrolyte solution. In some embodiments, each ion selective electrode is configured to detect an ion such as but not limited to sodium, potassium, calcium, magnesium, lithium, nitrate, hydrogen, sulfate, chloride, bicarbonate, phosphate or iodine.

In various embodiments, the non-conductive material of the substrate may be polyethylene terephthalate (PET), foil, glass, paper, silk or silicon dioxide. In some embodiments, the sensor includes two or more ion selective electrodes, and each of the ion selective electrodes is configured to detect a different ion. In various embodiments, the ion selective electrode material may be, but is not limited to, silver (Ag), silver/silver chloride (Ag/AgCl), gold (Au), platinum (Pt), aluminum (Al), chromium (Cr), nickel (Ni), iridium tin oxide (ITO), iridium oxide (IrOX), aluminum-doped zinc oxide (AZO), indium zinc oxide (IZO), fluorine doped tin oxide (FTO), poly(3,4-ethylenedioxythiophene) polystyrene sulfonate (PEDOT:PSS) or a conductive form of carbon.

The reference electrode material, according to various embodiments, may be (but is not limited to) silver-silver chloride (Ag/AgCl), calomel $Hg/Hg_2Cl_2$, mercury-mercury oxide Hg/HgO, mercury-mercurous sulfate $Hg/Hg_2SO_4$, silver-silver sulfate Ag/Ag2SO4, or copper-copper sulfate Cu/CuSO4. In various embodiments, the polymer of the mixture may include, but is not limited to, polydimethylsiloxane (PDMS), poly(vinyl alcohol) (PVA), poly(vinyl butyral) (PVB), poly(vinyl chloride) (PVC), polyurethane, and silk fibroin, and wherein the chloride-containing salt of the mixture is selected from the group consisting of potassium chloride (KCl), sodium chloride (NaCl), calcium chloride (CaCl2), or magnesium chloride (MgCl2).

The ion selective electrode(s) and the reference electrode may be deposited on the substrate using a method such as but not limited to screen printing, roll-to-roll, gravure, inkjet printing, photolithography or laser ablation. In some embodiments, the substrate, the ion selective electrode, the reference electrode, the insulating layer, the microfluidic layer and the cover layer are planar. In some embodiments, the ion sensor is configured for use with a substance such as but not limited to saliva, sweat, blood, serum, urine, water, wastewater, a beverage or a food.

In another aspect of the present application, a method for making an ion sensor may involve: providing a substrate comprising a non-conductive material; depositing at least one ion selective electrode including a ion selective electrode material on the substrate; depositing a reference electrode including a reference electrode material on the substrate; depositing a combination of a polymer and a chloride-containing salt deposited on the reference electrode material; placing an insulating layer over the at least one ion selective electrode and the reference electrode, the insulating layer comprising at least one opening for each of the at least one ion selective electrode and the reference electrode; placing a microfluidic layer over at least part of the insulating layer; and placing a cover layer over the microfluidic layer.

In some embodiments, the cover layer may include at least one exit pore and an inlet lip. In some embodiments, the method may further involve positioning a filter material layer on top of the insulation layer or between the microfluidic layer and the cover layer. The filter material layer may be made, for example, of filter paper, hydrophilic mesh, hydrophilic membrane or cotton batting. The method may also involve positioning an ion-selective membrane over part of the ion selective electrode. The ion-selective membrane may include an ionophore cocktail, such as those listed above. In some embodiments, the ion-selective membrane may include a ion/molecular imprinted polymer, functionalized membrane or antibody embedded polymer for detection of protein or antibody selective membrane that includes a linker to detect antibody. In some embodiments, the method may further involve positioning a transducing material layer between the ion selective electrode and the ion-selective membrane. The transducing material layer may include a material such as but not limited to those listed above.

In some embodiments, the ion sensor comprises two or more ion selective electrodes, and each of the ion selective electrodes is configured to detect a different ion. The ion selective electrode material may be, for example, silver (Ag), silver/silver chloride (Ag/AgCl), gold (Au), platinum (Pt), aluminum (Al), chromium (Cr), nickel (Ni), iridium tin oxide (ITO), iridium oxide (IrOX), aluminum-doped zinc oxide (AZO), indium zinc oxide (IZO), fluorine doped tin oxide (FTO), poly(3,4-ethylenedioxythiophene) polystyrene sulfonate (PEDOT:PSS) or a conductive form of carbon. The reference electrode material may be, for example, silver-silver chloride (Ag/AgCl), calomel Hg/Hg2Cl2, mercury-mercury oxide Hg/HgO, mercury-mercurous sulfate Hg/Hg2SO4, silver-silver sulfate Ag/Ag2SO4, or copper-copper sulfate Cu/CuSO4. In various embodiments, the ion selective electrode and the reference electrode are deposited on the substrate using a method such as but not limited to screen printing, roll-to-roll, gravure, inkjet printing, photolithography or laser ablation.

These and other aspects and embodiments are described in more detail below, in reference to the attached drawing figures.

DETAILED DESCRIPTION OF THE INVENTION

This application is generally directed to improved reference electrodes for ion sensors, as well as the ion sensors themselves and methods for making such sensors. The reference electrodes may be used in any of a number of different devices, such as but not limited to ion sensors, pH sensors, sweat patches, electrocardiogram (ECG) patches, and the like. Ion sensors described herein may be used for measuring ion content in any solution (fluid containing dissolved ions), such as but not limited to sweat, saliva, urine, tears or blood of a human or animal subject. The ion sensors described herein may be incorporated into or used with any suitable device. One example of such a device is a saliva test strip, directly used with a saliva measuring device that may test human or animal saliva for one or more of any number of different substances. Many other uses are possible, and the scope of the present application should not be interpreted as being limited by the examples described herein.

In some embodiments, saliva is tested using the ion sensors of the present application. According to various embodiments, saliva may be used to test for any suitable substance(s) or parameter(s). A few examples of such measurements include, but are not limited to, hydration, sodium, potassium, calcium, magnesium, lithium chlorides, phosphates, iron, oxalic acid and the like. In some embodiments, the system and method may be used to measure multiple substances or parameters, such as any combination of the substances/parameters just listed. And although it will not be repeated continuously throughout, any embodiment described for use with a human subject may alternatively be used for an animal subject (e.g., veterinary medicine, research, etc.). Similarly, any embodiment described herein may be used, or adapted for use, in testing any number of solutions, not only saliva.

Figure 1A:
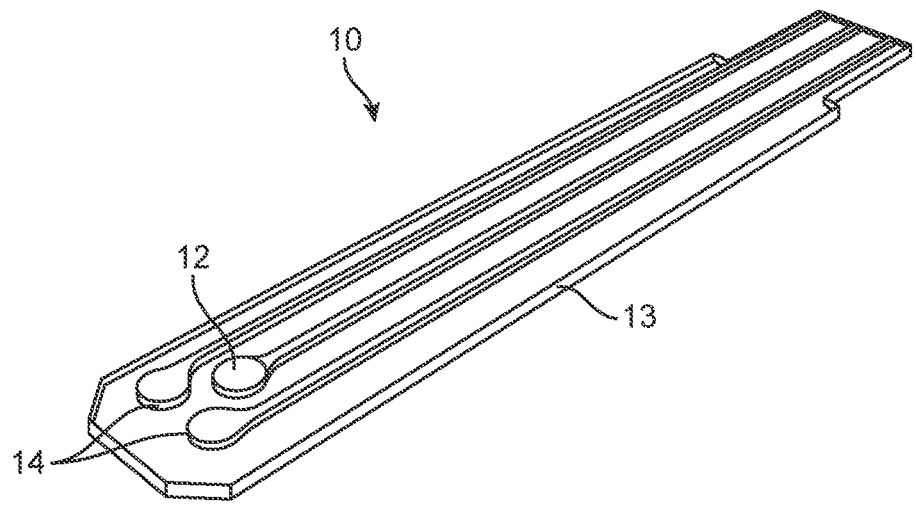
FIG. 1A is a perspective view of an electrode arrangement of an ion sensor, according to one embodiment.
Figure 1B:
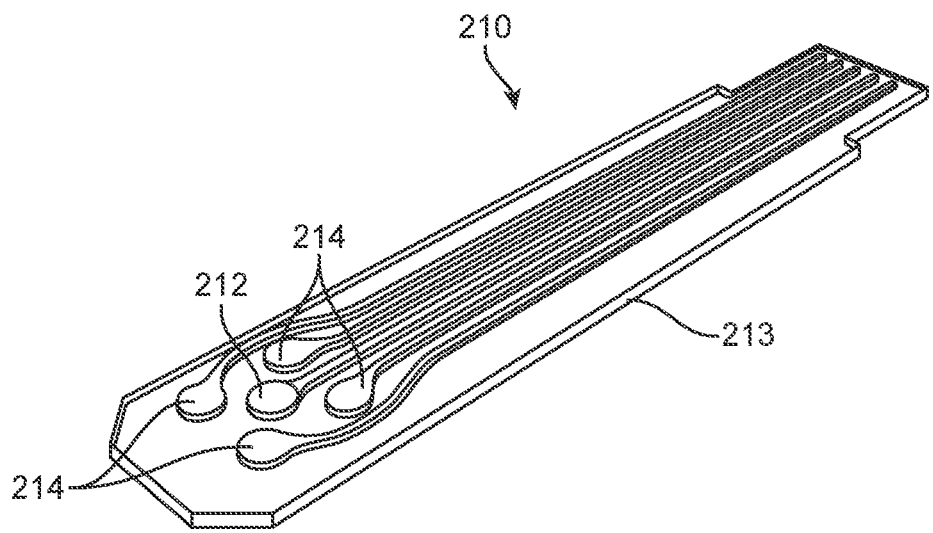
FIG. 1B is a perspective view of an electrode arrangement of an ion sensor, according to an alternative embodiment.

Referring now to FIG. 1A, one embodiment of an ion sensor 10 is configured for measuring ions and may be used for any purpose or for measuring any types of ions in any suitable solutions, according to various embodiments. The ion sensor 10 may include a substrate 13, a reference electrode 12, and two ion selective electrodes 14 (or "ISE 14"). In general, the ion sensor 10 will include at least one reference electrode 12 and at least one ISE 14. Some embodiments may include only one ISE 14, while alternative embodiments may contain multiple ISEs 14, for detecting multiple different ions. In various embodiments, more than two ISEs 14 may be used, and indeed any suitable number may be included on the ion sensor 10. The reference electrode 12 and the ISEs 14 are planar electrodes, which in this embodiment are screen printed on a substrate 13, made of any suitable non-conductive material, such as but not limited to polyethylene terephthalate (PET), foil, glass, paper, silk, silicon dioxide wafer or the like. In various embodiments, the substrate 13 may be flexible. In various alternative embodiments, any suitable printing method may be used for the electrodes 12, 14, such as but not limited to screen printing, roll-to-roll, gravure, inkjet printing, photolithography or laser ablation. Furthermore, in alternative embodiments, the reference electrode 12 and ISEs 14 may have any suitable shape, dimension, pattern or positional relationship relative to one another. The example positions of the electrodes 12, 14 shown in FIGS. 1A and 1B are merely examples and are not intended to limit the configuration of the electrodes 12, 14.

As mentioned above and shown in FIG. 1A, the ion sensor 10 may include at least one reference electrode 12. The reference electrode 12 is printed on a substrate 13, as discussed above, and may be made of any of a number of suitable materials, including but not limited to, silver-silver chloride (Ag/AgCl), calomel Hg/Hg2Cl2, mercury-mercury oxide Hg/HgO, mercury-mercurous sulfate Hg/Hg2SO4, silver-silver sulfate Ag/Ag2SO4, copper-copper sulfate Cu/CuSO4, or the like. On top of the reference electrode material, a polymer mixed with chloride-containing salt is printed. For example, the polymer may be, but is not limited to, polydimethylsiloxane (PDMS), poly(vinyl alcohol) (PVA), poly(vinyl butyral) (PVB), poly(vinyl chloride) (PVC), polyurethane, silk fibroin, or the like. The chloride-containing salt may be, but is not limited to, potassium chloride (KCl), sodium chloride (NaCl), calcium chloride (CaCl2), magnesium chloride (MgCl2), or the like. Alternatively, a saturated concentration of salt containing chloride in water may be dispersed onto the reference electrode 12. After the reference electrode 12 is dry, it can be covered with a thin layer of polymer.

The improved reference electrode 12 is planar, thus making it easy to manufacture using mass production techniques, cost effective and disposable. The reference electrode 12 may also be made in a very small size, so that the ion sensor 10 only requires a few microliters of the test solution. Additionally, the materials used to make the reference electrode 12 are biocompatible and can be used directly in-vivo. Another advantage of the reference electrode 12 is that, because it is a solid-state electrode, it does not require conditioning prior to use (for example no loading of KCl). The solid-state reference electrode 12 also has the advantage of long term stability, thus making it storable for long periods of time.

In one embodiment, the reference electrode 12 contains Ag/AgCl. This may be covered by a mixture of a polymer and potassium chloride (KCl), such as: (i) polydimethylsiloxane (PDMS) and KCl; or (ii) polyvinyl chloride (PVC) and KCl. In one PVC-based embodiment of the reference electrode 12, PVC powder is dissolved in cyclohexanone, and bis(2-ethylhexyl) sebacate (DOS) plasticizer is used. To dissolve KCl in cyclohexanone, a small amount of surfactant is added. The reference electrode 12 is dried for 30 minutes at 80 degrees Celsius or at room temperature. This reference electrode 12 does not require conditioning before use and thus may easily be made part of a disposable ion sensor 10.

In another embodiment, the reference electrode 12 contains Ag/AgCl that is covered by few microliters of 3 molar potassium chloride (KCl) and either dried in air at room temperature or by using vacuum evaporation. Then a few microliters of (i) polydimethylsiloxane (PDMS) or (ii) polyvinyl chloride (PVC) are drop-casted onto the electrode to cover the KCl. The reference electrode 12 is dried for 30 minutes at 80 degrees Celsius or at room temperature. This reference electrode 12 does not require conditioning before use and thus may easily be made part of a disposable ion sensor 10.

The ion sensor 10 may include as many ISEs 14 as desired and feasible, for the detection of specific ions. In some embodiments, an ISE 14 may be an ion selective field effective transistor (ISFET). Alternatively, the ISE 14 may be a metal oxide, such as ITO (combination of electrode materials and transducing materials) and may be used to detect ions with an ion selective membrane or pH without an ion selective membrane.

In various embodiments, the ISEs 14 may be printed on the substrate 13, as mentioned above regarding the reference electrode 12. Each ISE 14 may be made of any suitable metal that provides high electrical conductivity, such as but not limited to silver (Ag), silver/silver chloride (Ag/AgCl), gold (Au), platinum (Pt), aluminum (Al), chromium (Cr), nickel (Ni), or the like. The ISEs 14 may also include conductive metal oxides, such as but not limited to iridium tin oxide (ITO), iridium oxide (IrOX), aluminum-doped zinc oxide (AZO), indium zinc oxide (IZO), fluorine doped tin oxide (FTO), or the like. In addition, the material used to make the ISEs 14 may also be organic conductive material, such as but not limited to poly(3,4-ethylenedioxythiophene) polystyrene sulfonate (PEDOT:PSS) or any conductive form of carbon.

The ISEs 14 may be covered by an ion selective membrane (ISM) or a self-assembled monolayer. The ISM may be, for example, an ionophore cocktail, an ion/molecular imprinted polymer, an antibody selective membrane where a linker is embedded in the cocktail for specific antibody detection, or a surface of ISM functionalized with a linker or antibody embedded polymer for specific protein detection. Some examples of monatomic and polyatomic ions that may be detected by the ISEs 14 include, but are not limited to, $Na^+$, $K^+$, $Ca^{2+}$, $Mg^{2+}$, $Li^+$, $NO_3^-$, $H^+$ (pH), $SO_4^{2-}$, $Cl^-$, $HCO_3^-$, $PO_4^{3-}$ and $I^-$.

A layer of transducing material is printed in between the conductive material of the electrodes 12, 14 and the ion selective membrane. This transducing layer converts the activity of ions into electrons. The transducing material may be either p-type or n-type, examples of which include, but are not limited to, poly(3,4-ethylenedioxythiophene) polystyrene sulfonate (PEDOT:PSS), polypyrrole (PPy), polyaniline (PANI), and single or multi-walled carbon nanotubes. The transducing materials can be printed by any of the methods mentioned above for printing the electrodes 12, 14, as well as by electro-polymerization or drop-casting.

In one embodiment, the ISEs 14 are made of silver/silver chloride and carbon. Two microliters of poly(3,4-ethylenedioxythiophene) polystyrene sulfonate (PEDOT:PSS) are drop-casted onto each carbon electrode 14, and the electrodes 14 are allowed to dry. The deposition of the transducing layer (PEDOT:PSS) is not limited to drop-casting, but can include electropolymerization, aero-jetting, screen printing, R2R, transfer printing, or the like. Then, different ionophore cocktails relevant for each ion are drop-casted onto the ISEs 14 and allowed to dry at room temperature overnight.

The ionophore cocktails can be printed onto the substrate 13 using any of the methods mentioned above for printing the electrodes 12, 14, such as but not limited to screen printing, roll-to-roll, gravure, inkjet printing, and contact or non-contact (jet) dispensing. Alternatively, the ionophore cocktail can be poured into a dish and allowed dry for 24 hours to form a membrane. The membrane is then cut into small circular pieces and attached to the electrode 12, 14. Ionophore with conductive polymer can also be drop-casted or deposited using electropolymerization. Example ionophores include, but are not limited to, potassium ionophore, calcium ionophore, sodium ionophore, magnesium ionophore, hydrogen ionophore, nitrate ionophore, and ammonium ionophore. An ion/molecular imprinted polymer cocktail, antibody embedded polymer cocktail, or protein-ionophore cocktail can be printed using any of these methods. In addition, ion/molecular imprinted polymer mixed with carbon can be screen printed onto an ISE 14.

Referring now to FIG. 1B, another embodiment of an ion sensor 210 may include a substrate 213, a reference electrode 212, and four ion selective electrodes 214. The components of this embodiment of the ion sensor 210 (e.g., the substrate 213, reference electrode 212 and ISEs 214) may include any or all of the features, materials and/or the like described above, in relation to the embodiment of FIG. 1A. The example of FIG. 1B illustrates an alternative possible configuration and placement of ISEs 214, and many other numbers, configurations and placements of ISEs 214 are possible, in other alternative embodiments.

Figure 2:
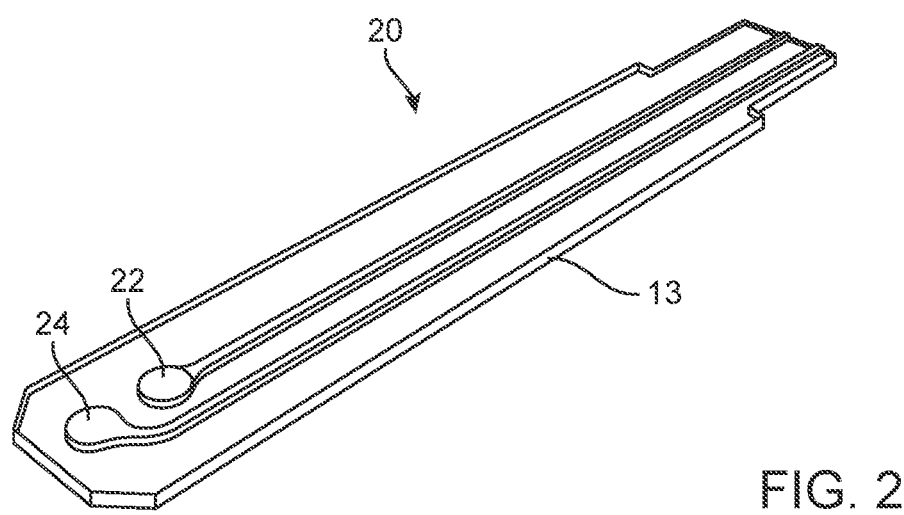
FIG. 2 is a perspective view of an electrode arrangement of a pH sensor, according to one embodiment.

Referring now to FIG. 2, one embodiment of a pH sensor 20 is illustrated in perspective view. In this embodiment, the pH sensor 20 includes a substrate 13, one reference electrode 22 and one ISE 24. In some embodiments, the ISE 24 may be an indium tin oxide (ITO) electrode. The pH sensor 20 may include any of the aspects and features of the ion sensor 10 described above (in relation to FIG. 1A), to provide a stable reference voltage generated by the reference electrode 22, for detecting pH in a sample substance.

Figure 3A:
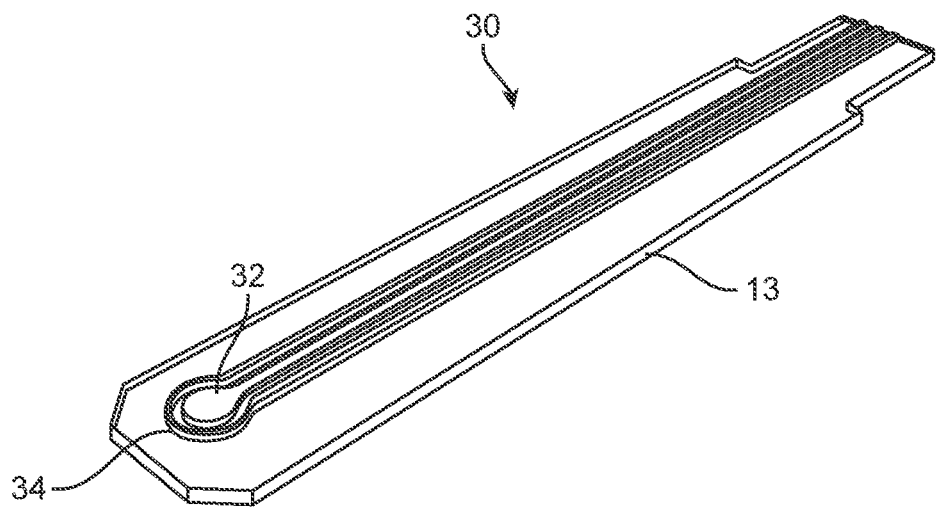
FIG. 3A is a perspective view of an electrode partially surrounded by an electrode guard, according to one embodiment.

FIG. 3A is a perspective view of part of a sensor 30, including a substrate 13, an ISE 32 (ion sensitive electrode) and an electrode guard 34. The guard 34 may be included in any of the sensor embodiments described herein and is configured to extend at least partially around one or more ISEs 32 to reduce undesired leakage current in measurement of ions or pH. In various embodiments, the guard 34 may be made of any high conductive material, such as but not limited to the ion selective electrode materials listed above.

Figure 3B:
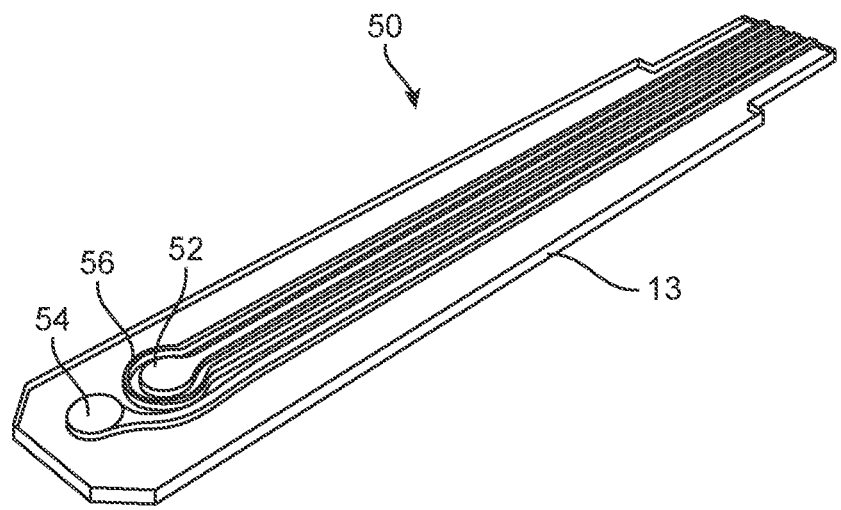
FIG. 3B is a perspective view of an ion sensor with an electrode guard, according to one embodiment.

FIG. 3B illustrates another embodiment of an ion sensor 50, which includes a substrate 53, a sensor guard 56 disposed around an ISE 52, and a reference electrode 54 outside the sensor guard 56. In other words, the sensor guard 56 is located between the reference electrode 54 and the ISE 52. In alternative embodiments, the guard 56, the reference electrode 54 and the ISE 52 may have any other suitable sizes, shapes and configurations.

Figure 4A:
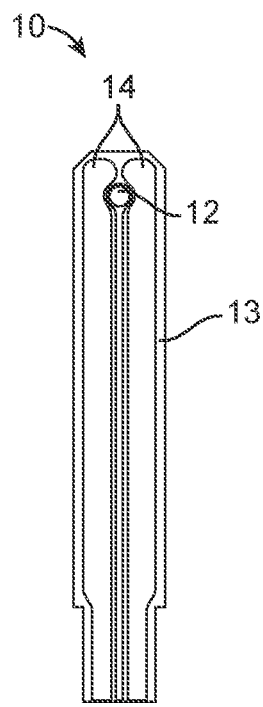
FIGS. 4A-4F are detailed top views of an ion sensor, in various stages of assembly, according to one embodiment.
Figure 4B:
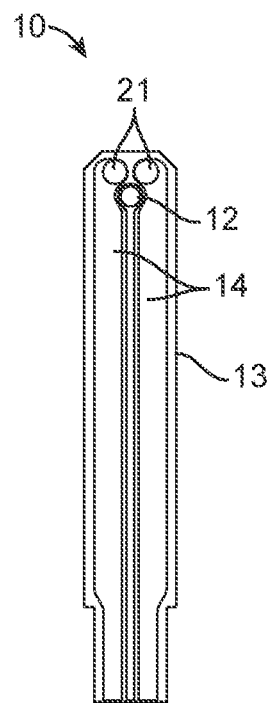
Figure 4C:
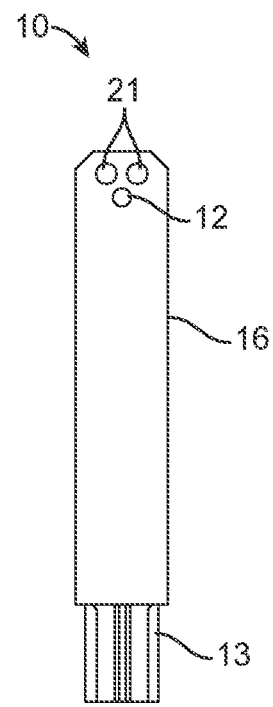

FIGS. 4A-4F are top views of the ion sensor 10 of FIG. 1A, showing additional detail in the various layers of the sensor 10, starting from the substrate 13 on the bottom layer and working upwards. FIG. 4A shows the electrodes 12, 14 printed onto the substrate 13. FIG. 4B shows a transducing material 21 screen printed on top of the ISEs 14. FIG. 4C shows an insulating layer 16 positioned over the electrodes 12, 14, with circular openings exposing part of each electrode 12, 14. The insulating material 16 may be any suitable material, including but not limited to PET adhesive materials.

Figure 4D:
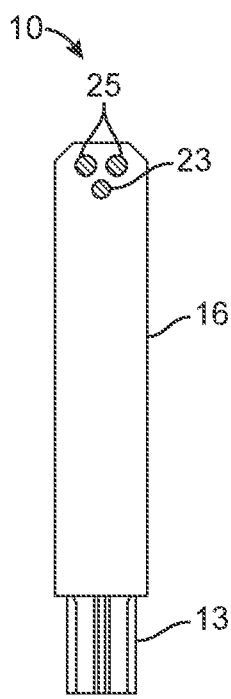
Figure 4E:
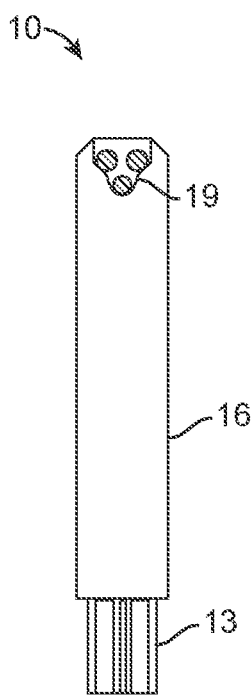
Figure 4F:
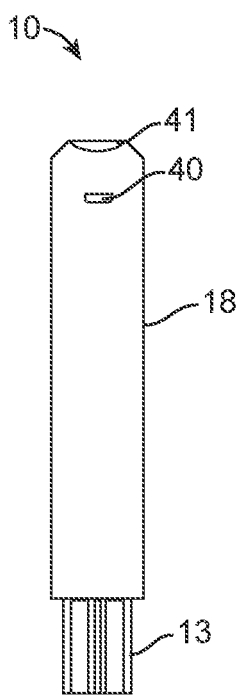

FIG. 4D shows the addition of a reference membrane 23 and two ion selective membranes 25. The reference membrane is disposed over the reference electrode 12 (not visible in FIG. 4D) and may be a polymer mixed with chloride containing salt, for example. FIG. 4E shows the addition of a filter or scaffold material 19 (e.g., filter paper, hydrophilic mesh, hydrophilic membrane, cotton batting (or "raw cotton" or "cotton wool")) disposed over part of the insulation layer 16 to help direct the flow of the test solution and to avoid discontinuity of the test solution in the channel. Finally, FIG. 4F shows the addition of a cover 18 with an exit pore 40 and an inlet lip 41 disposed over the ion sensor 10. The cover 18 material may be any suitable material, including but not limited to hydrophilic PET materials. The example in FIG. 4F also includes a microfluidic channel layer (not visible) positioned over the filter material 19. The microfluidic channel material may be any suitable material, including but not limited to PET adhesive materials.

Figure 5:
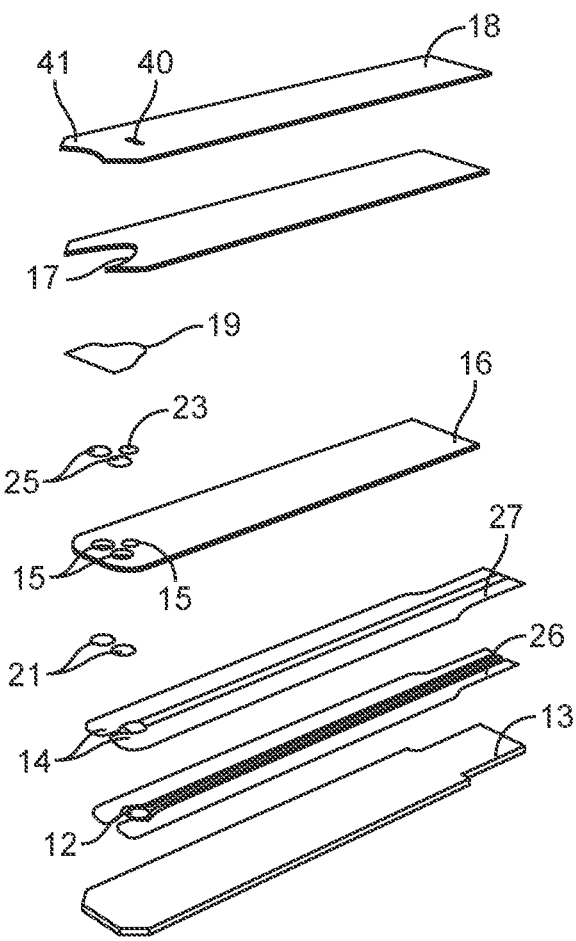
FIG. 5 is an exploded view of the ion sensor of FIGS. 4A-4F.

FIG. 5 is an exploded view of the ion sensor 10 of FIGS. 4A-4F, showing the layers described above. From bottom to top, the layers include: the substrate 13; the reference electrode 12, which is made of a silver-silver chloride layer 26; the ISEs 14, which are made of a carbon layer 27; the transducing material 21; the insulating layer 16 with the openings 15 for the electrodes 12, 14; the reference membrane 23 and ion selective membranes 25; the filter/scaffold material 19 (e.g., filter paper, mesh, cotton batting); the microfluidic channel layer 17; and the cover 18 with the exit pore 40 and inlet lip 41. These various layers may be stacked on one another to form the ion sensor 10. Alternative embodiments may include fewer layers, additional layers and/or differently configured layers, as needed.

Figure 6:
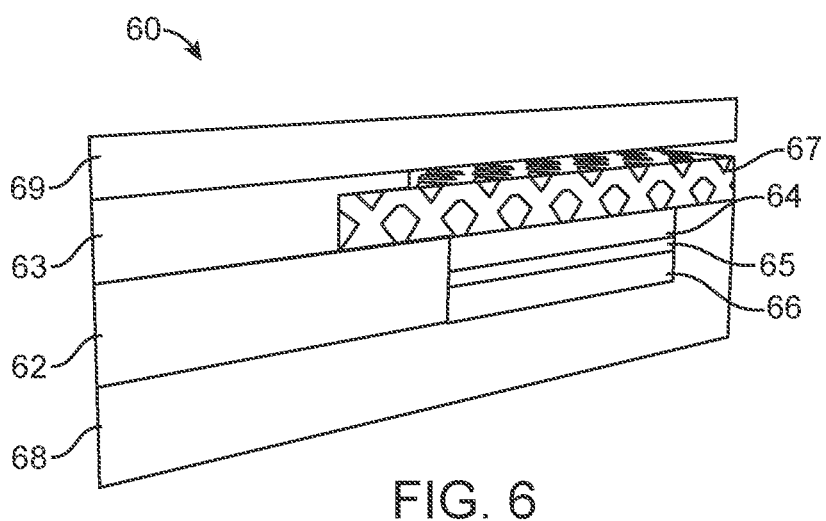
FIG. 6 is a cross-sectional view of an ion sensor, showing the ion selective electrode, according to one embodiment.

FIGS. 6-12 are side cross-sectional views showing different sections through various embodiments of an ion sensor or pH sensor, to further illustrate possible configurations and layering of various sensor embodiments. FIG. 6 is a side view of an ion sensor 60, showing a section of an ion selective electrode 66 of the sensor 60. This view illustrates a hydrophilic cover 69, a microfluidic channel 63, a filter material 67, an insulating layer 62, an ion selective membrane 64 (ISM), a transducing material 65, an ion selective electrode material 66, and a substrate 68. Any of the layers shown here may be made from any of the example materials discussed above or any other suitable materials.

Figure 7:
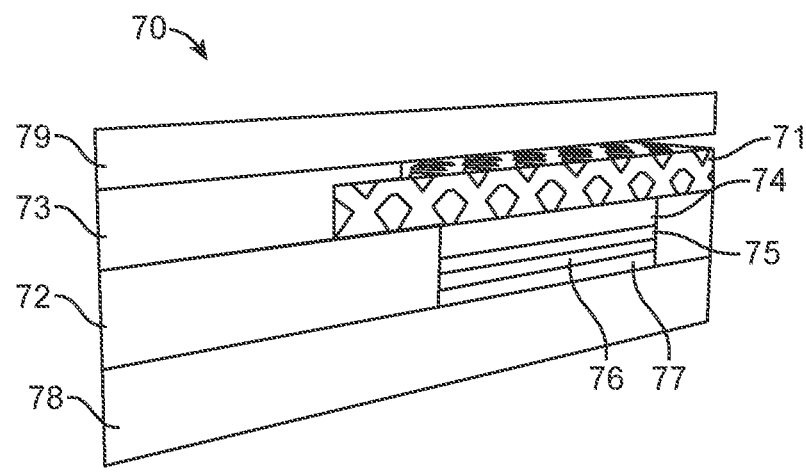
FIG. 7 is a cross-sectional view of an ion sensor, showing the ion selective electrode, according to an alternative embodiment.

FIG. 7 is a similar side cross-sectional view to that of FIG. 6, showing an ion sensor 70 at a section illustrating an ion selective electrode 76, 77. This view also illustrates a hydrophilic cover 79, microfluidic channel 73, filter material 71, an insulating layer 72, an ISM 74, a transducing material 75, and a substrate 78. The difference in this embodiment is that the ion selective electrode material includes two different layers of electrode material 76, 77, for example carbon 76 and silver/silver chloride 77.

Figure 8:
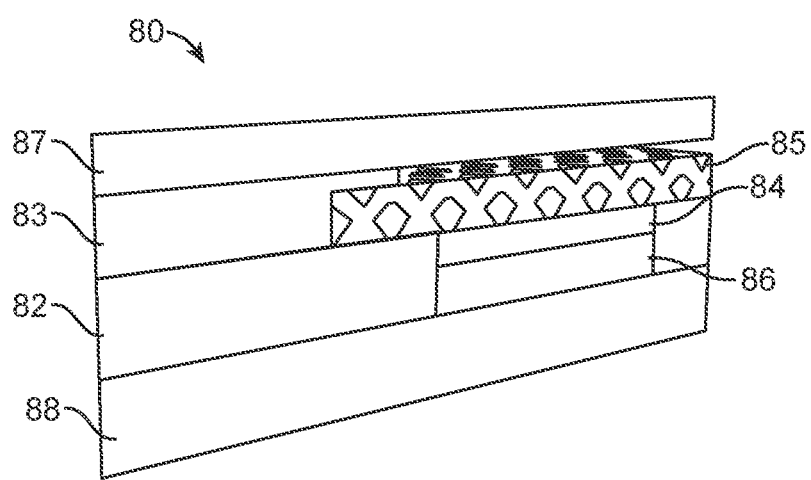
FIG. 8 is a cross-sectional view of an ion sensor, showing the ion selective electrode, according to another alternative embodiment.

FIG. 8 is a side cross-sectional view of another embodiment of an ion sensor 80, showing a hydrophilic cover 87, a microfluidic channel 83, a filter material 85, an insulating layer 82, an ISM 84, a metal oxide ion selective electrode 86 (e.g., ITO), and a substrate 88.

Figure 9:
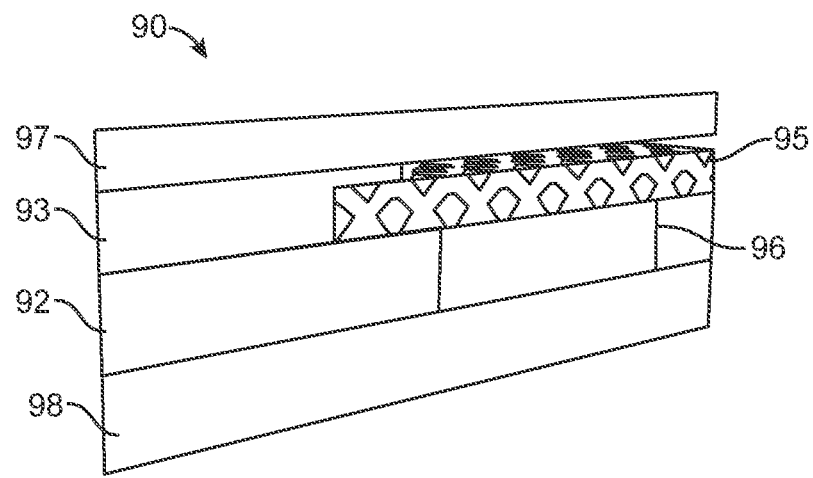
FIG. 9 is a cross-sectional view of a pH sensor, showing the ion selective electrode, according to one embodiment.

FIG. 9 is a side cross-sectional view of a pH sensor 90, showing a hydrophilic cover 97, a microfluidic channel 93, a filter material 95, an insulating layer 92, a metal oxide ion selective electrode 96 (e.g., ITO), and a substrate 98.

Figure 10:
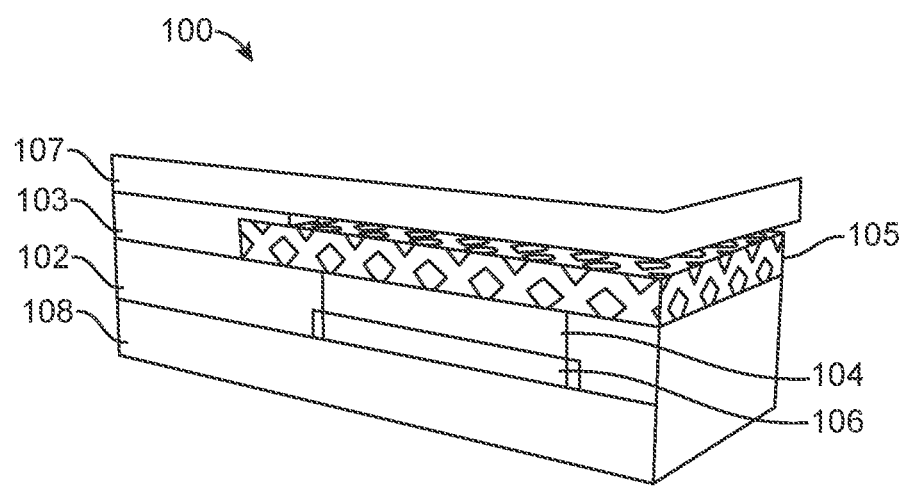
FIG. 10 is a cross-sectional view of an ion sensor, showing the reference electrode, according to one embodiment.

FIG. 10 is a side cross-sectional view of an ion sensor 100, showing a section through a reference electrode 106. Shown in this view are a hydrophilic cover 107, a microfluidic channel 103, a filter material 105, an insulating material 102, a reference membrane 104 (salt containing chloride covered with a polymer, e.g., KCl covered with PDMS), the reference electrode material 106 (e.g., Ag/AgCl), and a substrate 108.

Figure 11:
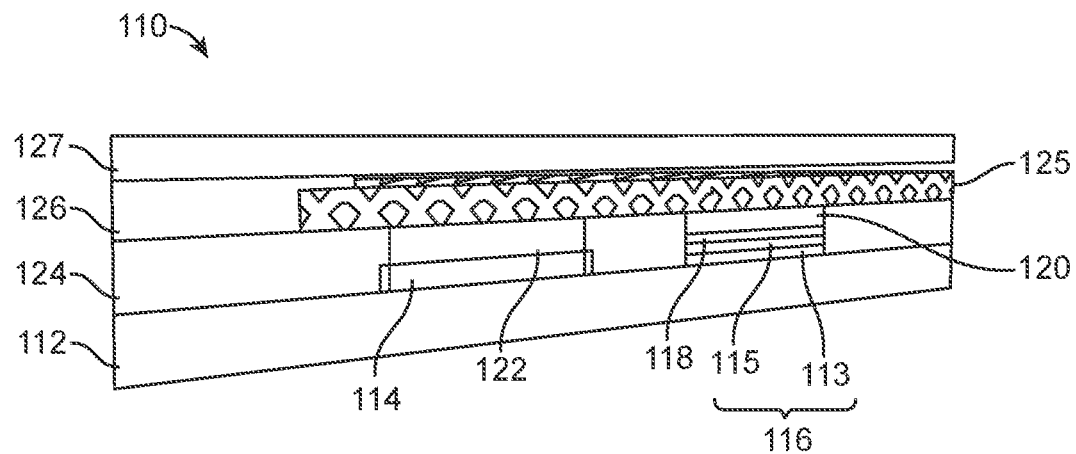
FIG. 11 is a cross-sectional view of an ion sensor, showing the ion selective electrode and the reference electrode, according to one embodiment.

FIG. 11 is a side cross-sectional view of an ion sensor 110 that shows both the reference electrode 114 and the ion selective electrode 116. This view includes a substrate 112, the ion selective electrode material 116 (for example silver/silver chloride 113 and carbon 115), transducing material 118, an ISM 120, a reference membrane 122 (salt containing chloride covered with a polymer, e.g., KCl covered with PDMS), an insulating layer 124, a filter material 125, a microfluidics layer 126 and a hydrophilic cover 127. Again, this is but one embodiment and is merely meant to illustrate one configuration for constructing an ion sensor 110.

Figure 12:
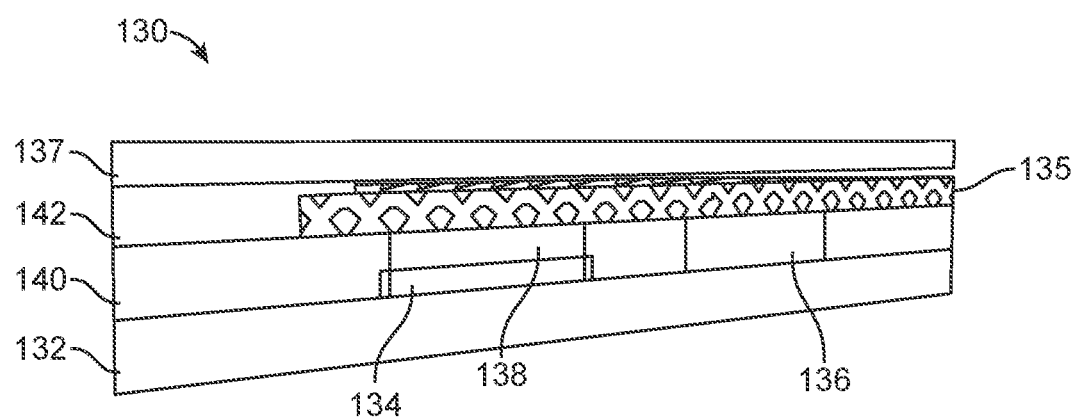
FIG. 12 is a cross-sectional view of a pH sensor, showing the ion selective electrode and the reference electrode, according to one embodiment.

FIG. 12 is a side cross-sectional view of pH sensor 130 that shows both the reference electrode 134 and the ion selective electrode 136. This view includes a substrate 132, a metal oxide ion selective electrode material 136, a reference membrane 138 (salt containing chloride covered with a polymer, e.g., KCl covered with PDMS), an insulating layer 140, microfluidics layer 142, a filter material 135 and a hydrophilic cover 137. Again, this is but one embodiment and is merely meant to illustrate one configuration for constructing a pH sensor 130.

The above described sensors have a number of unique, advantageous features. For example, the sensors include a solid state, biocompatible, planar reference electrode, which is disposable and does not require conditioning before use. Also, the sensor does not need to be calibrated just before use, as is typically the case with currently available ion sensors. Ion selective electrodes may contain metal oxide, such as ITO, with ion selective membranes, such as ionophore membranes and molecular imprinted polymers to detect ions. In some embodiments, the ion selective electrode is isolated using a guard, to reduce or eliminate leakage from reference electrode and undesired current paths.

In one embodiment, the microfluidics in the sensor allow it to be used to detect ions in saliva, where the sample is extracted directly from mouth, for example by placing one end of the sensor on the tongue. In another embodiment, the sensor can be used to detect ions in sweat, where the sample is extracted directly from skin (e.g., a sweat patch). In other embodiments, the microfluidics integrated with the sensor can be used to detect ions in blood, serum or urine. In addition to health applications, the sensors can be used in the fields of agriculture, aquaculture, arts, food and beverage, water, wastewater, livestock and manufacturing.

In some embodiments, the ion sensor can be integrated with a hydration sensor that measures osmolarity. Measuring osmolarity and ion concentration can be used to estimate the concentration of a major unknown ion. For example, major electrolytes in sweat are sodium, potassium and chloride. Measuring osmolarity and potassium of sweat can be used to estimate the concentration of sodium.

In one embodiment, the potentiometric measurements of ion sensors can be used for fluid detection. The potential of the ion selective electrode is floating when the fluid does not cover both the ISE and the reference electrode. Once the fluid covers both electrodes, the potential of the ion sensor goes to a pre-defined region by the calibration curve. This method may be used for fluid detection.

In another embodiment, the potentiometric measurements of ion sensors can be used to detect faulty sensors. For example, if one or more ion selective electrodes are short circuited with the reference electrode, the potential difference will be zero. Another example is, if ion selective electrode or reference electrode is partially or fully not covered, the potential difference will be lower than the pre-defined range by the calibration curve.

Experiment

Figure 13:
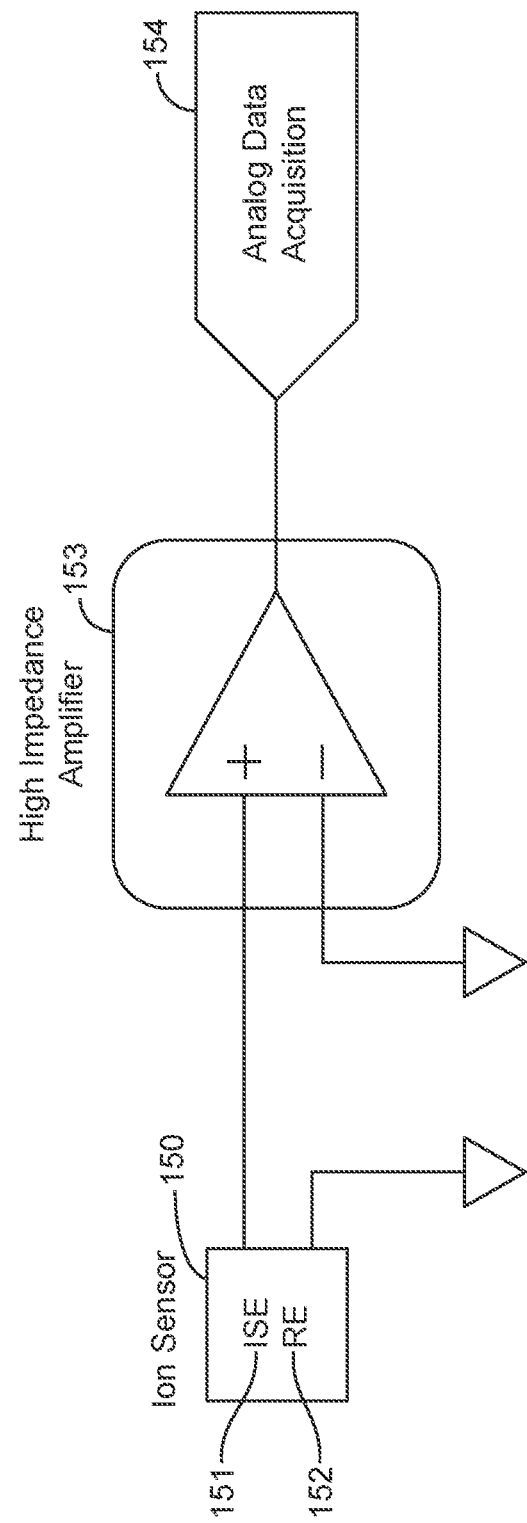
FIG. 13 is a simplified diagram of measurement setup, according to one embodiment.

Referring now to FIG. 13, a method for using an ion sensor 150 will now be described. The same or a similar method may also be used with a pH sensor. According to one example, the potential difference(s) between the ion selective electrode(s) 151 and the reference electrode 152 are measured (i.e., potentiometric measurements) by a high impedance amplifier 153. The measurement data is acquired by a high precision analog data acquisition system 154. In one experiment, potassium ion sensors were made as described above. They were immersed in standard KCl solutions, and KCl solutions spiked with 30 mM NaCl and 2.5 mM CaCl2. The concentrations of KCl solutions were 1 mM and 100 mM. The voltage difference of different disposable sensors immersed in above mentioned solutions were measured.

Figure 14:
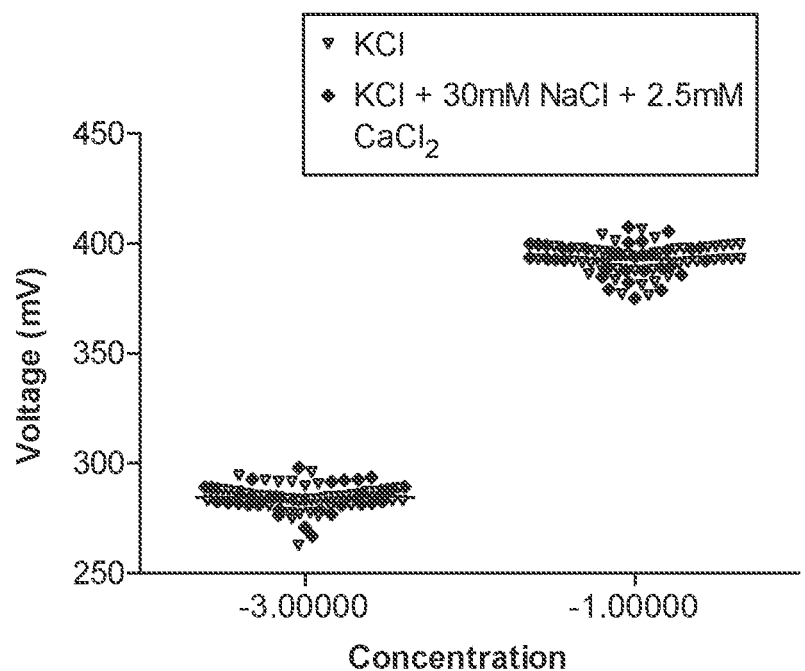
FIG. 14 is a chart illustrating voltage versus concentration of potassium ion in a solution measured using an potassium ion sensor during an experiment to show the selectivity of the sensor, according to one embodiment.

FIG. 14 shows the potential difference of the experimental sensors. The potential difference for 1 mM KCl and 1 mM KCl spiked with 30 mM NaCl and 2.5 mM CaCl2 overlaps. Similarly, at 100 mM KCl and 100 mM KCl spiked with 30 mM NaCl and 2.5 mM CaCl2 overlaps. This shows that interfering ions do not change the potential of the sensors and show the stability of the reference electrode 152 and specificity of the ion selective electrode 151.

Figure 15:
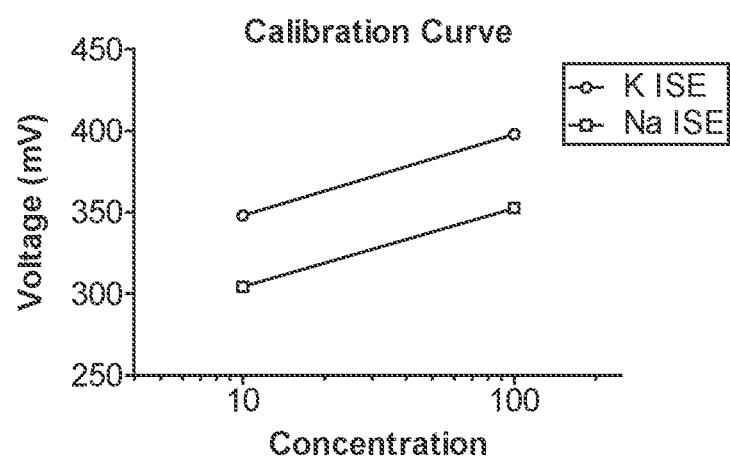
FIG. 15 is a voltage versus concentration chart illustrating the calibration curves for potassium and sodium ion sensors, measured using a potassium and sodium ion sensor during an experiment, according to one embodiment.
Figure 16:
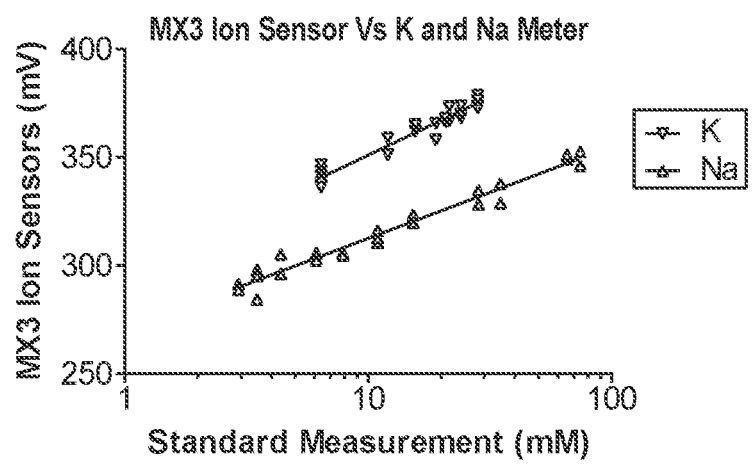
FIG. 16 is a voltage versus concentration chart illustrating concentrations of potassium and sodium ions in sweat and saliva samples, measured using a potassium and sodium ion sensor during an experiment, according to one embodiment.
Figure 17:
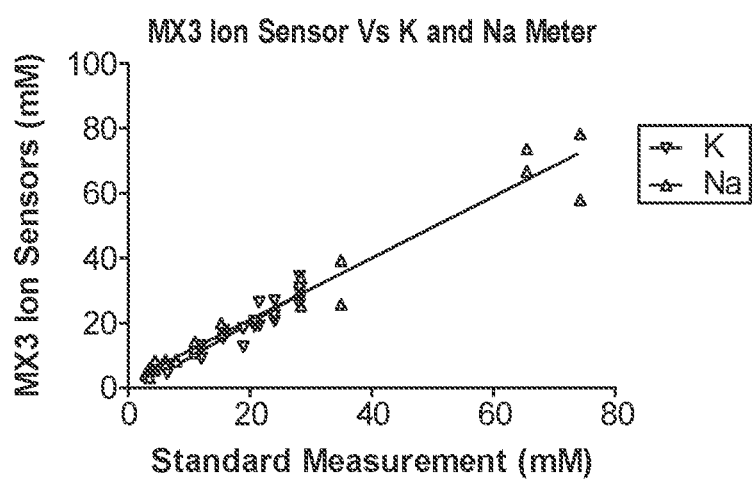
FIG. 17 is a chart illustrating the estimated concentration of potassium and sodium ions in sweat and saliva samples from FIGS. 15 and 16.

FIG. 15A illustrates results of another experiment, using an ion sensor with potassium ion selective electrode, sodium ion selective electrode and a reference electrode. The measurements of potassium and sodium ions in a solution with potassium, sodium, calcium and chloride ions are shown in FIG. 15A. The concentration of solutions are 10 mM NaCl+ 10 mM KCl+2.5 mM CaCl2 and 100 mM NaCl+100 mM KCl+2.5 mM CaCl2.

FIG. 15B shows the measurement of potassium and sodium ions in sweat and saliva samples using the above described ion sensors. These measured potential differences are plotted against the concentration of ions measured from a standard ion meter. The correlation of the above-mentioned ion sensor measurements with a standard ion meter is above 0.9 (R-square). The calibration curves in FIG. 15A were used to estimate the ion concentration in sweat and saliva samples and shown in FIG. 15C. The correlation of measured ion concentrations using the above-mentioned ion sensor with a standard ion meter is above 0.9 (R-square).

The above description is intended to be a complete description of embodiments of improved reference electrodes for ion sensors, as well as the ion sensors themselves and methods for making such sensors. It is meant to be a description of examples only and is not intended to limit the scope of the invention.

We claim:

1. An ion sensor, comprising:
   a substrate comprising a non-conductive material;
   at least one ion selective electrode comprising an ion selective electrode material deposited on the substrate;
   a reference electrode, comprising:
      a reference electrode material deposited on the substrate; and
      a combination of a chloride-containing salt and a polymer deposited on the reference electrode material;
   an insulating layer placed over the at least one ion selective electrode and the reference electrode, the insulating layer comprising at least one opening for each of the at least one ion selective electrode and the reference electrode;
   an ion-selective membrane disposed over at least a part of the ion selective electrode material; wherein the ion-selective membrane comprises an ionophore protein cocktail configured to detect a specific antibody;
   a microfluidic layer placed over at least part of the insulating layer; and
   a cover layer placed over the microfluidic layer.

2. The ion sensor of claim 1, wherein the cover layer comprises:
   at least one exit pore; and
   an inlet lip.

3. The ion sensor of claim 1, further comprising at least one filter material layer positioned at least one of above the insulating layer or between the microfluidic layer and the cover layer, wherein the at least one filter material layer comprises a material selected from the group consisting of filter paper, hydrophilic mesh, hydrophilic membrane, and cotton batting.

4. The ion sensor of claim 1, wherein the ionophore protein cocktail comprises an ionophore selected from the group consisting of potassium ionophore, calcium ionophore, sodium ionophore, magnesium ionophore, hydrogen ionophore, nitrate ionophore, and ammonium ionophore.

5. The ion sensor of claim 1, further comprising a transducing material layer disposed between the ion selective electrode material and the ion-selective membrane.

6. The ion sensor of claim 5, wherein the transducing material layer comprises a material selected from the group consisting of poly(3,4-ethylenedioxythiophene) polystyrene sulfonate (PEDOT:PSS), polypyrrole (PPy), polyaniline (PANI), and carbon nanotubes.

7. The ion sensor of claim 1, further comprising at least one additional ion selective electrode configured to detect a pH of a solution, and wherein the additional ion selective electrode material comprises a metal oxide.

8. The ion sensor of claim 1, further comprising at least one additional ion selective electrode comprising a metal oxide and an ion-selective membrane configured to detect ions of an electrolyte solution.

9. The ion sensor of claim 1, wherein each of the at least one ion selective electrodes is configured to detect an ion selected from the group consisting of sodium, potassium, calcium, magnesium, lithium, nitrate, hydrogen, sulfate, chloride, bicarbonate, phosphate, and iodine.

10. The ion sensor of claim 1, wherein the non-conductive material of the substrate is selected from the group consisting of polyethylene terephthalate (PET), foil, glass, paper, silk, and silicon dioxide.

11. The ion sensor of claim 1, wherein the at least one ion selective electrode comprises two or more ion selective electrodes, and wherein each of the ion selective electrodes is configured to detect a different ion.

12. The ion sensor of claim 1, wherein the ion selective electrode material is selected from the group consisting of silver (Ag), silver/silver chloride (Ag/AgCl), gold (Au), platinum (Pt), aluminum (Al), chromium (Cr), nickel (Ni), iridium tin oxide (ITO), iridium oxide (IrOX), aluminum-doped zinc oxide (AZO), indium zinc oxide (IZO), fluorine doped tin oxide (FTO), poly(3,4-ethylenedioxythiophene) polystyrene sulfonate (PEDOT:PSS), and a conductive form of carbon.

13. The ion sensor of claim 1, wherein the reference electrode material is selected from the group consisting of silver-silver chloride (Ag/AgCl), calomel Hg/Hg2Cl2, mercury-mercury oxide Hg/HgO, mercury-mercurous sulfate Hg/Hg2SO4, silver-silver sulfate Ag/Ag2SO4, and copper-copper sulfate Cu/CuSO4.

14. The ion sensor of claim 1, wherein the polymer of the reference electrode is selected from the group consisting of polydimethylsiloxane (PDMS), poly(vinyl alcohol) (PVA), poly(vinyl butyral) (PVB), poly(vinyl chloride) (PVC), polyurethane, and silk fibroin, and wherein the chloride-containing salt of the reference electrode material is selected from the group consisting of potassium chloride (KCl), sodium chloride (NaCl), calcium chloride (CaCl2), and magnesium chloride (MgCl2).

15. The ion sensor of claim 1, wherein the at least one ion selective electrode and the reference electrode are deposited on the substrate using a method selected from the group consisting of screen printing, roll-to-roll, gravure, inkjet printing, photolithography, and laser ablation.

16. The ion sensor of claim 1, wherein the substrate, the at least one ion selective electrode, the reference electrode, the insulating layer, the microfluidic layer, and the cover layer are planar.

17. The ion sensor of claim 1, wherein the ion sensor is configured for use with a substance selected from the group consisting of saliva, sweat, blood, serum, urine, water, wastewater, a beverage, and a food.

18. A method for making ion sensor, the method comprising:
   providing a substrate comprising a non-conductive material;

forming at least one ion selective electrode on the substrate by:
  depositing at least one ion selective electrode material on the substrate; and
  positioning an ion-selective membrane over part of the at least one ion selective electrode material;
forming a reference electrode on the substrate by:
  depositing a reference electrode material on the substrate; and
  depositing a combination of a polymer and a chloride-containing salt on the reference electrode material;
placing an insulating layer over the at least one ion selective electrode and the reference electrode, the insulating layer comprising at least one opening for each of the at least one ion selective electrode and the reference electrode;
placing a microfluidic layer over at least part of the insulating layer; and
placing a cover layer over the microfluidic layer;
wherein the ion-selective membrane comprises an ionophore protein cocktail configured to detect a specific antibody.

19. The method of claim 18, further comprising providing the cover layer with at least one exit pore and an inlet lip.

20. The method of claim 18, further comprising positioning at least one filter material layer at least one of above the insulating layer or between the microfluidic layer and the cover layer, wherein the at least one filter material layer comprises a material selected from the group consisting of filter paper, hydrophilic mesh, hydrophilic membrane and cotton batting.

21. The method of claim 18, wherein the ionophore protein cocktail comprises an ionophore selected from the group consisting of potassium ionophore, calcium ionophore, sodium ionophore, magnesium ionophore, hydrogen ionophore, nitrate ionophore, and ammonium ionophore.

22. The method of claim 18, further comprising positioning a transducing material layer between the at least one ion selective electrode material and the ion-selective membrane.

23. The method of claim 22, wherein the transducing material layer comprises a material selected from the group consisting of poly(3,4-ethylenedioxythiophene) polystyrene sulfonate (PEDOT:PSS), polypyrrole (PPy), polyaniline (PANI), and carbon nanotubes.

24. The method of claim 18, further comprising forming at least one additional ion selective electrode configured to detect a pH of a solution, and wherein the at least one additional ion selective electrode material comprises a metal oxide.

25. The method of claim 18, wherein the at least one ion selective electrode is configured to detect an ion selected from the group consisting of sodium, potassium, calcium, magnesium, lithium, nitrate, hydrogen, sulfate, chloride, bicarbonate, phosphate, and iodine.

26. The method of claim 18, wherein the non-conductive material of the substrate is selected from the group consisting of polyethylene terephthalate (PET), foil, glass, paper, silk, and silicon dioxide.

27. The method of claim 18, wherein the at least one ion selective electrode comprises two or more ion selective electrodes, and wherein each of the ion selective electrodes is configured to detect a different ion.

28. The method of claim 18, wherein the ion selective electrode material is selected from the group consisting of silver (Ag), silver/silver chloride (Ag/AgCl), gold (Au), platinum (Pt), aluminum (Al), chromium (Cr), nickel (Ni), iridium tin oxide (ITO), iridium oxide (IrOX), aluminum-doped zinc oxide (AZO), indium zinc oxide (IZO), fluorine doped tin oxide (FTO), poly(3,4-ethylenedioxythiophene) polystyrene sulfonate (PEDOT:PSS), and a conductive form of carbon.

29. The method of claim 18, wherein the reference electrode material is selected from the group consisting of silver-silver chloride (Ag/AgCl), calomel $Hg/Hg_2Cl_2$, mercury-mercury oxide Hg/HgO, mercury-mercurous sulfate $Hg/Hg_2SO_4$, silver-silver sulfate $Ag/Ag_2SO_4$, and copper-copper sulfate $Cu/CuSO_4$.

30. The method of claim 18, wherein the polymer of the reference electrode is selected from the group consisting of polydimethylsiloxane (PDMS), poly(vinyl alcohol) (PVA), poly(vinyl butyral) (PVB), poly(vinyl chloride) (PVC), polyurethane, and silk fibroin, and wherein the chloride-containing salt of the reference electrode is selected from the group consisting of potassium chloride (KCl), sodium chloride (NaCl), calcium chloride ($CaCl_2$), and magnesium chloride ($MgCl_2$).

31. The method of claim 18, wherein the at least one ion selective electrode and the reference electrode are deposited on the substrate using a method selected from the group consisting of screen printing, roll-to-roll, gravure, inkjet printing, photolithography, and laser ablation.

* * * * *